United States Patent [19]

Hasegawa et al.

[11] Patent Number: 5,416,213
[45] Date of Patent: May 16, 1995

[54] TETRAVINYLPYRAZINE COMPOUND, METHOD FOR PREPARING SAME AND ELECTROLUMINESCENT ELEMENT AND NON-LINEAR OPTICAL MATERIAL USING SAME

[75] Inventors: Masaki Hasegawa, Tokyo; Masao Nohara, Chiba; Yutaka Ohashi, Kanagawa, all of Japan

[73] Assignee: Mitsui Toatsu Chemicals, Inc., Tokyo, Japan

[21] Appl. No.: 890,204

[22] Filed: May 29, 1992

[30] Foreign Application Priority Data

May 30, 1991 [JP] Japan .................................. 3-127112
Jun. 13, 1991 [JP] Japan .................................. 3-141728
Feb. 19, 1992 [JP] Japan .................................. 4-031715

[51] Int. Cl.⁶ .................. C07D 241/12; C07D 401/06; C07D 405/06; C07D 409/06
[52] U.S. Cl. ..................................... 544/405; 544/336; 544/410; 428/690
[58] Field of Search ........................ 544/336, 405, 410

[56] References Cited

U.S. PATENT DOCUMENTS 4,676,834 6/1987 Treybig ............................ 106/14.15
5,013,840 5/1991 Teshirogi ............................ 544/336

OTHER PUBLICATIONS

Hasegawa et al, Chemical Abstracts, vol. 109, No. 231062 (1988) (Abstract for JP62-201874, Sep. 5, 1987).
Nohara et al, *Chemistry Letters*, pp. 189–190 (1990).
Chemical Abstracts, vol. 102, No. 14, 1985, Columbus, Ohio. Abs. #122445u O. Nobuhiro et al. "Fluorescence polarization . . ." p. 588.
World Patents Index Latest, Section Ch, Week 31, Class A, AN 90–14 23578 & JP-A-2 163 144, Jun. 22, 1990.
World Patents Index Latest, Section Ch, Week 22, Class A, AN 90-169291 & JP-A-2 112 178, Apr. 24, 1990.
Patent Abstracts of Japan, vol. 013, No. 156 (C-585) & JP-A-63 3122 347 Dec. 20, 1988.
Patent Abstracts of Japan, vol. 015, No. 238 (C-0841) & JP-A-03 074 499 Mar. 29, 1991.

*Primary Examiner*—Emily Bernhardt
*Attorney, Agent, or Firm*—Millen, White, Zelano, & Branigan

[57] ABSTRACT

Herein disclosed are a tetravinylpyrazine compound which has high light-emitting efficiency and thermal stability and which is represented by the following general formula (1):

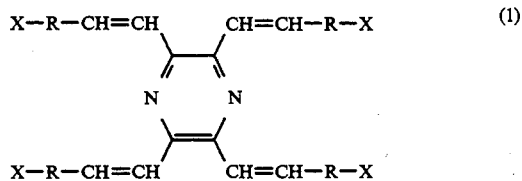

wherein R represents an aromatic ring or a heterocyclic ring; X represents a hydrogen atom, an aliphatic hydrocarbon group, an alicyclic hydrocarbon group, an aromatic hydrocarbon group, a halogen atom, a hydroxyl group, an alkoxy group, a carboxyl group, an alkoxycarbonyl group, an acylamino group, a dialkylamino group, a nitro group, an acyloxy group or an acyloxycarbonyl group; a method for preparing the tetravinylpyrazine; and electroluminescent elements and non-linear optical materials using the pyrazine compound.

6 Claims, 6 Drawing Sheets

TETRAVINYLPYRAZINE COMPOUND, METHOD FOR PREPARING SAME AND ELECTROLUMINESCENT ELEMENT AND NON-LINEAR OPTICAL MATERIAL USING SAME

BACKGROUND OF THE INVENTION

1. Field of the Invention

The present invention relates to a tetravinylpyrazine compound having a vinyl bond at the 2-, 3-, 5- and 6-positions of the pyrazine ring respectively, a method for preparing the pyrazine compound and an electroluminescent element and nonlinear optical material obtained using the pyrazine compound.

2. Description of the Prior Art

Due to the recent marked progress in the information industry and information-oriented society, there has been increasing requirements for members capable of displaying information which exhibit higher quality. Among elements for such members, electroluminescent elements (EL elements) which make use of an electroluminescence (EL) phenomenon have become of major interest lately because of their excellent properties such as good visibility.

There have been developed and already put on the market so-called intrinsic type EL elements such as those in which inorganic fine particles are dispersed in a matrix of an organic substance and those obtained by sandwiching inorganic thin films of, for instance, znS between insulating thin films. However, these elements require high driving voltages and it is difficult to obtain elements which emit lights having wavelengths falling within, for instance, the blue range.

There have been known injection-type EL elements in addition to the intrinsic-type ones. These injection-type elements emit light through recombination of electrons and positive holes which have been injected into p-n junctions of, for instance, semiconductors. These elements are, for instance, characterized in that they can be operated at a low DC voltage and that they have high efficiencies of converting electric energy into light. Inorganic crystalline semiconductors such as GaP have principally been used to produce these injection-type EL elements. However, they suffer from the problems that they are limited in the colors of emitted lights and that it is difficult to enlarge the area of the elements.

For this reason, there have been recent been requirements for the development of techniques for producing EL elements which operate at a low driving voltage, can emit lights of any desired colors and have a large surface area.

Recently, there have been proposed novel injection-type EL elements which make use of thin films of organic compounds (see C. T. Tang, Appl. Phys. Lett., 1987, 51(12), p. 193) and have attracted much attention. This is because the colors of emitted lights can arbitrarily be selected due to the use of organic substances, the elements can be operated at a low DC voltage and an element having a large area can be obtained by a thin film-forming method such as a deposition or coating method. However, there still remains some problems. For example, the EL elements comprising the thin films of these organic compounds suffer from a problem of reduction in the brightness of the emitted lights when they are operated over an extended time, i.e., the problem of so-called deterioration.

One of the sources of such deterioration may be the degeneration of the organic compounds due to generation of heat. This is because, the efficiency of converting an electric energy into light is presently on the order of several percentages and most of the energy is converted into heat. Therefore, it is necessary to develop an element which makes use of an organic compound having good heat resistance and light-emitting efficiency in order to eliminate the problem of deterioration.

Incidentally, there have been proposed, as materials for organic thin layer EL elements, 2,5-distyryl pyrazine derivatives (see M. Nohara, Chem. Lett., 1990, p. 189), but the EL elements obtained from these materials suffer from the problem of low stability.

Further, non-linear optical devices which make use of tertiary non-linear optical effects such as optical bistable elements and optical gate switches have been anticipated as key devices for future ultrahigh speed electronic data processing systems. In order to improve the quality of these devices, it is necessary to develop non-linear optical materials which have a high non-linear susceptibility (hereinafter referred to as "$\chi^{(3)}$") and high speed responsibility.

Inorganic materials have conventionally been employed, but organic materials having E electron conjugated systems have attracted much attention recently because of their high responsibility and high non-linear susceptibility due to the presence of $\pi$ electrons. There have been known, for instance, polymer systems such as polyacetylene and polydiacetylene; and low molecular systems such as azomethines. All of these compounds have one-dimensional $\pi$ electron conjugation and the maximum $\chi^{(3)}$ thereof is $10^{-8}$ esu due to the response of these electron systems. However, this value is substantially determined on the basis of the presence or absence of the one-dimensional $\pi$ electron conjugation and is not dependent upon the chemical structure of a specific compound selected. Thus, there has not yet been discovered any organic materials having $\chi^{(3)}$ substantially greater than $10^{-8}$ esu. Moreover, the quality indices of non-linear optical devices are given by $\chi^{(3)}/(\alpha\tau)$ (wherein $\tau$ is a response speed and $\alpha$ is the coefficient of light absorption) and, therefore, the indices must be increased as high as possible. However, there is a limit in the quality of these organic materials having one-dimensional $\pi$ electron conjugation. For this reason, it has been required for the discovery of other materials different from the foregoing materials.

SUMMARY OF THE INVENTION

Accordingly, an object of the present invention is to provide specific tetravinylpyrazine compounds which are preferably used as organic optoelectric functional materials for electroluminescent elements and non-linear optical elements and are excellent in thermal stability.

Another object of the present invention is to provide an EL element which makes use of a thin film comprising a specific tetravinylpyrazine compound as a light-emitting layer and has a high light-emitting efficiency and excellent thermal stability.

A still further object of the present invention is to provide a non-linear optical material which comprises a specific tetravinylpyrazine compound and exhibits high non-linear optical properties.

The inventors of this invention have conducted various studies to accomplish the foregoing objects, have found that specific tetravinylpyrazine compounds show excellent properties favorable for use as organic optoelectric functional materials and thus have completed the present invention.

According to an aspect of the present invention, there is provided a tetravinylpyrazine compound represented by the following general formula (1):

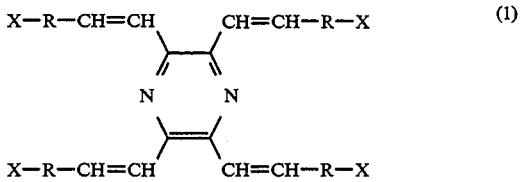

wherein R represents an aromatic ring or a heterocyclic ring; X represents a hydrogen atom, an aliphatic hydrocarbon group, an alicyclic hydrocarbon group, an aromatic hydrocarbon group, a halogen atom, a hydroxyl group, an alkoxy group, a carboxyl group, an alkoxycarbonyl group, an acylamino group, a dialkylamino group, a nitro group, an acyloxy group or an acyloxycarbonyl group.

According to a second aspect of the present invention, there is provided a method for preparing a tetravinylpyrazine compound represented by the foregoing general formula (1) which comprises the step of reacting 2,3,5,6-tetramethyl pyrazine represented by the following formula (2):

with an aldehyde compound represented by the following general formula (3):

X-R-CHO          (3)

(wherein R represents an aromatic ring or a heterocyclic ring; X represents a hydrogen atom, an aliphatic hydrocarbon group, an alicyclic hydrocarbon group, an aromatic hydrocarbon group, a halogen atom, a hydroxyl group, an alkoxy group, a carboxyl group, an alkoxycarbonyl group, an acylamino group, a dialkylamino group or a nitro group) in the presence of an acid anhydride.

According to a third aspect of the present invention, there is provided an electroluminescent element having a monolayer or multilayer thin film structure comprising at least one light-emitting layer; a positive hole-transporting layer and a light-emitting layer which are laminated in this order; or a positive hole-transporting layer, a light-emitting layer and an electron-transporting layer which are laminated in this order, the mono- or multilayer thin film structure being positioned between two electrodes, wherein the light-emitting layer is a thin film comprising a tetravinylpyrazine compound represented by the foregoing general formula (1).

According to a fourth aspect of the present invention, there is provided a non-linear optical material used for producing a non-linear optical device, which comprises a tetravinylpyrazine compound represented by the foregoing general formula (1).

DESCRIPTION OF THE PREFERRED EMBODIMENTS

Figure 1:
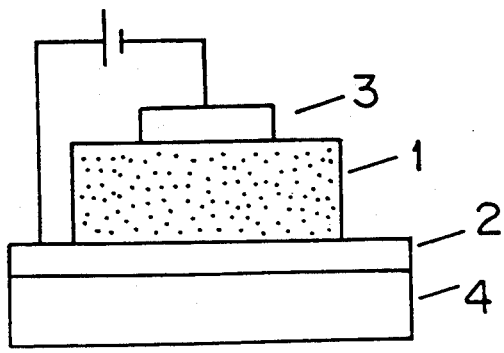
FIGS. 1 to 4 are, respectively, schematic cross sectional views showing examples of the structures of different EL elements according to the present invention.

In the compounds of the present invention represented by the foregoing general formula (1), the aromatic ring represented by the substituent R is, for example, a benzene, naphthalene, anthracene or pyrene ring. The heterocyclic ring comprises, as hetero atoms, oxygen, nitrogen and/or sulfur and if the ring comprises at least two hetero atoms, these hetero atoms may be the same or different. Examples of the heterocyclic rings are pyridine, quinoline, furan, thiophene, benzoxazole and benzothiazole.

In the compounds of the present invention represented by the foregoing general formula (1), the substituent X represents a hydrogen atom, an aliphatic hydrocarbon group, an alicyclic hydrocarbon group, an aromatic hydrocarbon group, a halogen atom, a hydroxyl group, an alkoxy group, a carboxyl group, an alkoxycarbonyl group, an acylamino group, a dialkylamino group, a nitro group, an acyloxy group or an acyloxycarbonyl group. Examples of these substituents are methyl and ethyl groups for the aliphatic hydrocarbon group; cyclopentyl and cyclohexyl groups for the alicyclic hydrocarbon group; phenyl and naphthyl groups for the aromatic hydrocarbon group; chlorine and fluorine atoms for the halogen atom; methoxy and ethoxy groups for the alkoxy group; methoxycarbonyl and ethoxycarbonyl groups for the alkoxycarbonyl group; acetylamino group for the acylamino group; and dimethylamino and diethylamino groups for the dialkylamino group. Moreover, it is also possible to prepare compounds of Formula (1) wherein at least two X's are linked to R in addition to those in which only one X is bonded to R.

Typical examples of the compounds of the present invention will be given below.

Examples of the compounds of Formula (1) wherein x is a hydrogen atom include those in which R is an aromatic ring such as 2,3,5,6-tetrakis[2-(phenyl)vinyl]- pyrazine, 2,3,5,6-tetrakis[2-(1-naphthyl)vinyl]pyrazine, 2,3,5,6-tetrakis[2-(2-naphthyl)vinyl]pyrazine, 2,3,5,6-tetrakis[2-(1-anthryl) vinyl]pyrazine, 2,3,5,6-tetrakis[2-(2-anthryl)vinyl]pyrazine and 2,3,5,6-tetrakis[2-(9-anthryl)vinyl]pyrazine and those in which R is a heterocyclic ring such as 2,3,5,6-tetrakis[2-(2-pyridyl) vinyl]pyrazine, 2,3,5,6-tetrakis[2-(3-pyridyl)vinyl]pyrazine, 2,3,5,6-tetrakis[2-(4-pyridyl)vinyl]pyrazine, 2,3,5,6-tetrakis[2-(2-quinolyl)vinyl]pyrazine, 2,3,5,6-tetrakis[2-(3-quinolyl)vinyl]pyrazine, 2,3,5,6-tetrakis[2-(4-quinolyl) vinyl]pyrazine, 2,3,5,6-tetrakis[2-(5-quinolyl)vinyl]pyrazine, 2,3,5,6-tetrakis[2-(6-quinolyl)vinyl]pyrazine, 2,3,5,6-tetrakis[2-(7-quinolyl)vinyl]pyrazine, 2,3,5,6-tetrakis[2-(8-quinolyl)vinyl]pyrazine, 2,3,5,6-tetrakis[2-(2-furyl) vinyl]pyrazine, 2,3,5,6-tetrakis[2-(3-furyl)vinyl]pyrazine, 2,3,5,6-tetrakis[2-(2-thienyl)vinyl]pyrazine, 2,3,5,6-tetrakis[2-(3-thienyl)vinyl]pyrazine, 2,3,5,6-tetrakis[ 2-(benzoxazyl)vinyl]pyrazine and 2,3,5,6-tetrakis[2- (benzothiazyl) vinyl]pyrazine.

Examples of the compounds of Formula (1) wherein X is a substituent other than hydrogen atom and R is an aromatic ring include those in which X is an aliphatic hydrocarbon group such as 2,3,5,6-tetrakis[2-(p-tolyl)-vinyl]pyrazine, 2,3,5,6-tetrakis[2-(o-tolyl)vinyl]pyrazine, 2,3,5,6-tetrakis[2-(m-tolyl) vinyl]pyrazine, 2,3,5,6-tetrakis [2-(p-ethylphenyl) vinyl]pyrazine, 2,3,5,6-tetrakis[2-(o-ethylphenyl) vinyl]pyrazine, 2,3,5,6-tetrakis[2-(m-ethylphenyl) vinyl]pyrazine, 2,3,5,6-tetrakis[2-(p-propylphenyl) vinyl]pyrazine, 2,3,5,6-tetrakis[2-(o-propylphenyl) vinyl]pyrazine and 2,3,5,6-tetrakis[2-(m-propylphenyl) vinyl]pyrazine; those in which X is an alicyclic hydrocarbon group such as 2,3,5,6-tetrakis[2-(2-cyclohexylphenyl) vinyl]pyrazine and 2,3,5,6-tetrakis[2-(3-cyclohexylphenyl) vinyl]pyrazine; those in which X is an aromatic hydrocarbon group such as 2,3,5,6-tetrakis[2-(2-biphenyl)vinyl]pyrazine, 2,3,5,6-tetrakis [2-(3-biphenyl)vinyl]pyrazine and 2,3,5,6-tetrakis[2-(4-biphenyl)vinyl]pyrazine; those in which X is a halogen atom such as 2,3,5,6-tetrakis[2-(4-chlorophenyl) vinyl]pyrazine, 2,3,5,6-tetrakis [2-(3-chlorophenyl) vinyl]pyrazine and 2,3,5,6-tetrakis [2-(2-chlorophenyl) vinyl]pyrazine; those in which X is a hydroxyl group such as 2,3,5,6-tetrakis[2-(4-hydroxyphenyl)vinyl]pyrazine, 2,3,5,6-tetrakis [2-(3-hydroxyphenyl)vinyl]pyrazine and 2,3,5,6-tetrakis[2-(2-hydroxyphenyl)vinyl]pyrazine; those in which X is an alkoxy group such as 2,3,5,6-tetrakis[2-(4-methoxyphenyl) vinyl]pyrazine, 2,3,5,6-tetrakis[2-(3-methoxyphenyl) vinyl]pyrazine and 2,3,5,6-tetrakis[2-(2-methoxyphenyl) vinyl]pyrazine; those in which X is a carboxyl group such as 2,3,5,6-tetrakis[2-(2-carboxyphenyl)vinyl]pyrazine, 2,3,5,6-tetrakis[2-(3-carboxyphenyl)vinyl]pyrazine and 2,3,5,6-tetrakis[2-(4-carboxyphenyl)vinyl]pyrazine; those in which X is an alkoxycarbonyl group such as 2,3,5,6-tetrakis[2-(2-methoxycarbonylphenyl)vinyl]-pyrazine, 2,3,5,6-tetrakis[2-(3-methoxycarbonylphenyl)vinyl]pyrazine, 2,3,5,6-tetrakis[2-(4-methoxycarbonylphenyl)vinyl]pyrazine, 2,3,5,6-tetrakis[2-(2-ethoxycarbonylphenyl)vinyl]pyrazine, 2,3,5,6-tetrakis [2-(3-ethoxycarbonylphenyl)vinyl]pyrazine and 2,3,5,6-tetrakis[2-(4-ethoxycarbonylphenyl)vinyl]pyrazine; those in which X is an acylamino group such as 2,3,5,6-tetrakis[2-(2-a cetylaminophenyl)vinyl]pyrazine, 2,3,5,6-tetrakis[2-(3-acetylaminophenyl)vinyl]pyrazine and 2,3,5,6-tetrakis[2-(4-acetylaminophenyl)vinyl]pyrazine; those in which X is a dialkylamino group such as 2,3,5,6-tetrakis[2-(2-dimethylaminophenyl)vinyl]pyrazine, 2,3,5,6-tetrakis[2-(3-dimethylaminophenyl)vinyl]-pyrazine, 2,3,5,6-tetrakis[2-(4-dimethylaminophenyl)-vinyl]pyrazine, 2,3,5,6-tetrakis[2-(2-diethylaminophenyl)vinyl]pyrazine, 2,3,5,6-tetrakis[2-(3-diethylaminophenyl)vinyl]pyrazine and 2,3,5,6-tetrakis[2-(4-diethylaminophenyl)vinyl]pyrazine; and those in which X is a nitro group such as 2,3,5,6-tetrakis[2-(2-nitrophenyl) vinyl]pyrazine, 2,3,5,6-tetrakis[2-(3-nitrophenyl) vinyl]pyrazine and 2,3,5,6-tetrakis[2-(4-nitrophenyl) vinyl]pyrazine.

Examples of compounds of Formula (1) wherein R is a heterocyclic ring include those in which X is an aliphatic hydrocarbon group such as 2,3,5,6-tetrakis[2-((3-methyl)-2-pyridyl)vinyl]pyrazine, 2,3,5,6-tetrakis[2-(((4-methyl)-2-pyridyl)vinyl]pyrazine, 2,3,5,6-tetrakis[2-((5-methyl)-2-pyridyl)vinyl]pyrazine, 2,3,5,6-tetrakis[2-((6-methyl)-2-pyridyl)vinyl]pyrazine, 2,3,5,6-tetrakis[2-((2-methyl)-3-pyridyl)vinyl]pyrazine, 2,3,5,6-tetrakis[2-((4-methyl)-3-pyridyl)vinyl]pyrazine, 2,3,5,6-tetrakis[2-((5-methyl)-3-pyridyl)vinyl]pyrazine, 2,3,5,6-tetrakis[2-((6-methyl)-3-pyridyl)vinyl]pyrazine, 2,3,5,6-tetrakis[2-((2-methyl)-4-pyridyl)vinyl]pyrazine, 2,3,5,6-tetrakis[2-((3-methyl)-4-pyridyl)vinyl]pyrazine, 2,3,5,6-tetrakis[2-((3-ethyl)-2-pyridyl)vinyl]pyrazine, 2,3,5,6-tetrakis[2-((4-ethyl)-2-pyridyl)vinyl]pyrazine, 2,3,5,6-tetrakis[2-((5-ethyl)-2-pyridyl)vinyl]pyrazine, 2,3,5,6-tetrakis[2-((6-ethyl)-2-pyridyl)vinyl]pyrazine, 2,3,5,6-tetrakis[2-((2-ethyl)-3-pyridyl)vinyl]pyrazine, 2,3,5,6-tetrakis[2-((4-ethyl)-3-pyridyl)vinyl]pyrazine, 2,3,5,6-tetrakis[2-((5-ethyl)-3-pyridyl)vinyl]pyrazine, 2,3,5,6-tetrakis[2-((6-ethyl)-3-pyridyl)vinyl]pyrazine, 2,3,5,6-tetrakis[2-((2-ethyl)-4-pyridyl) vinyl]pyrazine and 2,3,5,6-tetrakis[2-((3-ethyl)-4-pyridyl) vinyl]pyrazine; those in which X is an alicyclic hydrocarbon group such as 2,3,5,6-tetrakis[2-((3-cyclohexyl)-2-pyridyl) vinyl]pyrazine, 2,3,5,6-tetrakis[2-((4-cyclohexyl)-2-pyridyl) vinyl]pyrazine, 2,3,5,6-tetrakis[2-((5-cyclohexyl)-2-pyridyl) vinyl]pyrazine, 2,3,5,6-tetrakis[2-((6-cyclohexyl)-2-pyridyl) vinyl]pyrazine, 2,3,5,6-tetrakis[2-((2-cyclohexyl)-3-pyridyl) vinyl]pyrazine, 2,3,5,6-tetrakis[2-((4-cyclohexyl)-3-pyridyl) vinyl]pyrazine, 2,3,5,6-tetrakis[2-((5-cyclohexyl)-3-pyridyl) vinyl]pyrazine, 2,3,5,6-tetrakis[2-((6-cyclohexyl)-3-pyridyl) vinyl]pyrazine, 2,3,5,6-tetrakis[2-((2-cyclohexyl)-4-pyridyl) vinyl]pyrazine and 2,3,5,6-tetrakis[2-((3-cyclohexyl)-4-pyridyl)vinyl]pyrazine; those in which X is an aromatic hydrocarbon group such as 2,3,5,6-tetrakis[2-((3-phenyl)-2-pyridyl)vinyl]pyrazine, 2,3,5,6-tetrakis[2-((4-phenyl)-2-pyridyl)vinyl]pyrazine, 2,3,5,6-tetrakis[2-((5-phenyl)-2-pyridyl)vinyl]pyrazine, 2,3,5,6-tetrakis[2-((6-phenyl)-2-pyridyl)vinyl]pyrazine, 2,3,5,6-tetrakis[2-((2-phenyl)-3-pyridyl)vinyl]pyrazine, 2,3,5,6-tetrakis[2-((4-phenyl)-3-pyridyl)vinyl]pyrazine, 2,3,5,6-tetrakis[2-((5-phenyl)-3-pyridyl)vinyl]pyrazine, 2,3,5,6-tetrakis[2-((6-phenyl)-3-pyridyl)vinyl]pyrazine, 2,3,5,6-tetrakis[2-((2-phenyl)-4-pyridyl)vinyl]pyrazine, 2,3,5,6-tetrakis[2-((3-phenyl)-4-pyridyl)vinyl]pyrazine, 2,3,5,6-tetrakis[2-((3-(1-naphthyl))-2-pyridyl)vinyl]pyrazine, 2,3,5,6-tetrakis[2-((4-(1-naphthyl))-2-pyridyl)vinyl]pyrazine, 2,3,5,6-tetrakis[2-((5-(1-naphthyl))-2-pyridyl)vinyl]-pyrazine, 2,3,5,6-tetrakis[2-((6-(1-naphthyl))-2-pyridyl)-vinyl]pyrazine, 2,3,5,6-tetrakis[2-((2-(1-naphthyl))-3-pyridyl)vinyl]pyrazine, 2,3,5,6-tetrakis[2-((4-(1-naphthyl))-3-pyridyl)vinyl]pyrazine, 2,3,5,6-tetrakis[2-((5-(1-naphthyl))-3-pyridyl)vinyl]pyrazine, 2,3,5,6-tetrakis[2-((6-(1-naphthyl))-3-pyridyl)vinyl]pyrazine, 2,3,5,6-tetrakis[2-((2-(1-naphthyl))-4-pyridyl)vinyl]-pyrazine, 2,3,5,6-tetrakis[2-((3-(2-naphthyl))-4-pyridyl)-vinyl]pyrazine, 2,3,5,6-tetrakis[2-((3-(2-naphthyl))-2- pyridyl)vinyl]pyrazine, 2,3,5,6-tetrakis[2-((4-(2-naphthyl))- 2-pyridyl)vinyl]pyrazine, 2,3,5,6-tetrakis[2-((5-(2-naphthyl))-2-pyridyl)vinyl]pyrazine, 2,3,5,6-tetrakis[2-((6-(2-naphthyl))-2-pyridyl)vinyl]pyrazine, 2,3,5,6-tetrakis[2-((2-(2-naphthyl))-3-pyridyl)vinyl]pyrazine, 2,3,5,6-tetrakis[2-((4-(2-naphthyl))-3-pyridyl)vinyl]pyrazine, 2,3,5,6-tetrakis[2-((5-(2-naphthyl))-3-pyridyl)vinyl]pyrazine, 2,3,5,6-tetrakis[2-((6-(2-naphthyl))-3-pyridyl)vinyl]pyrazine, 2,3,5,6-tetrakis[2-((2-(2-naphthyl))-4-pyridyl)vinyl]pyrazine and 2,3,5,6-tetrakis[2-((3-(2-naphthyl))-4-pyridyl)vinyl]pyrazine; th6Se in which X is a halogen atom such as 2,3,5,6-tetrakis[2-((3-chloro)-2-pyridyl) vinyl]pyrazine, 2,3,5,6-tetrakis[2-((4-chloro)-2-pyridyl) vinyl]pyrazine, 2,3,5,6-tetrakis[2-((5-chloro)-2-pyridyl) vinyl]pyrazine, 2,3,5,6-tetrakis[2-((6-chloro)-2-pyridyl) vinyl]pyrazine, 2,3,5,6-tetrakis[2-((2-chloro)-3-pyridyl) vinyl]pyrazine, 2,3,5,6-tetrakis[2-((4-chloro)-3-pyridyl) vinyl]pyrazine, 2,3,5,6-tetrakis[2-((5-chloro)-3-pyridyl) vinyl]pyrazine, 2,3,5,6-tetrakis[2-((6-chloro)-3-pyridyl) vinyl]pyrazine, 2,3,5,6-tetrakis[2-((2-chloro)-4-pyridyl) vinyl]pyrazine and 2,3,5,6-tetrakis[2-((3-chloro)-4-pyridyl) vinyl]pyrazine; those in which X is a hydroxyl group such as 2,3,5,6-tetrakis[2-((3-hydroxy)-2-pyridyl)vinyl]pyrazine, 2,3,5,6-tetrakis[2-((4-hydroxy)-2-pyridyl)vinyl]pyrazine, 2,3,5,6-tetrakis[2-((5-hydroxy)-2-pyridyl)vinyl]pyrazine, 2,3,5,6-tetrakis[2-((6-hydroxy)-2-pyridyl)vinyl]pyrazine, 2,3,5,6-tetrakis[2-((2-hydroxy)-3-pyridyl)vinyl]pyrazine, 2,3,5,6-tetrakis[2-((4-hydroxy)-3-pyridyl)vinyl]pyrazine, 2,3,5,6-tetrakis[2-((5-hydroxy)-3-pyridyl)vinyl]pyrazine, 2,3,5,6-tetrakis[2-((6-hydroxy)-3-pyridyl)vinyl]pyrazine, 2,3,5,6-tetrakis[2-((2-hydroxy)-4-pyridyl)vinyl]pyrazine and 2,3,5,6-tetrakis[2-((3-hydroxy)-4-pyridyl)vinyl]pyrazine; those in which X is an alkoxy group such as 2,3,5,6-tetrakis[2-((3-methoxy)-2-pyridyl)vinyl]pyrazine, 2,3,5,6-tetrakis[2-((4-methoxy)-2-pyridyl)vinyl]pyrazine, 2,3,5,6-tetrakis[2-((5-methoxy)-2-pyridyl)vinyl]pyrazine, 2,3,5,6-tetrakis[2-((6-methoxy)-2-pyridyl)vinyl]pyrazine, 2,3,5,6-tetrakis[2-((2-methoxy)-3-pyridyl)vinyl]pyrazine, 2,3,5,6-tetrakis[2-((4-methoxy)-3-pyridyl)vinyl]pyrazine, 2,3,5,6-tetrakis[2-((5-methoxy)-3-pyridyl)vinyl]pyrazine, 2,3,5,6-tetrakis[2-((6-methoxy)-3-pyridyl)vinyl]pyrazine, 2,3,5,6-tetrakis[2-((2-methoxy)-4-pyridyl)vinyl]pyrazine and 2,3,5,6-tetrakis[2-((3-methoxy)-4-pyridyl)vinyl]pyrazine; those in which X is a carboxyl group such as 2,3,5,6-tetrakis[2-((3-carboxy)-2-pyridyl)vinyl]pyrazine, 2,3,5,6-tetrakis[2-((4-carboxy)-2-pyridyl)vinyl]pyrazine, 2,3,5,6-tetrakis[2-((5-carboxy)-2-pyridyl)vinyl]pyrazine, 2,3,5,6-tetrakis[2-((6-carboxy)-2-pyridyl)vinyl]pyrazine, 2,3,5,6-tetrakis[2-((2-carboxy)-3-pyridyl)vinyl]pyrazine, 2,3,5,6-tetrakis[2-((4-carboxy)-3-pyridyl)vinyl]pyrazine, 2,3,5,6-tetrakis[2-((5-carboxy)-3-pyridyl)vinyl]pyrazine, 2,3,5,6-tetrakis[2-((6-carboxy)-3-pyridyl)vinyl]pyrazine, 2,3,5,6-tetrakis[2-((2-carboxy)-4-pyridyl)vinyl]pyrazine and 2,3,5,6-tetrakis[2-((3-carboxy)-4-pyridyl)vinyl]pyrazine; those in which X is an alkoxycarbonyl group such as 2,3,5,6-tetrakis[2-((3-methoxycarbonyl)-2-pyridyl)vinyl]pyrazine, 2,3,5,6-tetrakis[2-((4-methoxycarbonyl) -2-pyridyl)vinyl]pyrazine, 2,3,5,6-tetrakis[2-((5-methoxycarbonyl)-2-pyridyl)vinyl]pyrazine, 2,3,5,6-tetrakis[ 2-((6-methoxycarbonyl)-2-pyridyl)vinyl]pyrazine, 2,3,5,6-tetrakis[2-((2-methoxycarbonyl)-3-pyridyl)vinyl]pyrazine, 2,3,5,6-tetrakis[2-((4-methoxycarbonyl)-3-pyridyl) vinyl]pyrazine, 2,3,5,6-tetrakis[2-((5-methoxycarbonyl)-3-pyridyl)vinyl]pyrazine, 2,3,5,6-tetrakis[2-((6-methoxycarbonyl) -3-pyridyl)vinyl]pyrazine, 2,3,5,6-tetrakis[2-((2-methoxycarbonyl)-4-pyridyl)vinyl]pyrazine and 2,3,5,6-tetrakis[2-((3-methoxycarbonyl)-4-pyridyl)vinyl]pyrazine; those in which X is an acylamino group such as 2,3,5,6-tetrakis[2-((3-acetylamino)-2-pyridyl)vinyl]pyrazine, 2,3,5,6-tetrakis[2-((4-acetylamino)-2-pyridyl)vinyl]pyrazine, 2,3,5,6-tetrakis[2-((5-acetylamino)-2-pyridyl)vinyl]pyrazine, 2,3,5,6-tetrakis[2-((6-acetylamino)-2-pyridyl)vinyl]pyrazine, 2,3,5,6-tetrakis[2-((2-acetylamino)-3-pyridyl)vinyl]pyrazine, 2,3,5,6-tetrakis[2-((4-acetylamino)-3-pyridyl)vinyl]pyrazine, 2,3,5,6-tetrakis[2-((5-acetylamino)-3-pyridyl)vinyl]pyrazine, 2,3,5,6-tetrakis[2-((6-acetylamino)-3-pyridyl)vinyl]pyrazine, 2,3,5,6-tetrakis[2-((2-acetylamino)-4-pyridyl)vinyl]pyrazine and 2,3,5,6-tetrakis[2((3-acerylamino)-4-pyridyl)vinyl]pyrazine; those in which X is a dialkylamino group such as 2,3,5,6-tetrakis[2-((3-dimethylamino)-2-pyridyl)vinyl]pyrazine, 2,3,5,6-tetrakis[2-((4-dimethylamino)-2-pyridyl)vinyl]pyrazine, 2,3,5,6-tetrakis[2-((5-dimethylamino)-2-pyridyl)vinyl]pyrazine, 2,3,5,6-tetrakis[2-((6-dimethylamino)-2-pyridyl)vinyl]pyrazine, 2,3,5,6-tetrakis[2-((2-dimethylamino)-3-pyridyl)vinyl]pyrazine, 2,3,5,6-tetrakis[2-((4-dimethylamino)-3-pyridyl)vinyl]pyrazine, 2,3,5,6-tetrakis[2-((5-dimethylamino)-3-pyridyl)vinyl]pyrazine, 2,3,5,6-tetrakis[2-((6-dimethylamino)-3-pyridyl)vinyl]pyrazine, 2,3,5,6-tetrakis[2-(( 2-dimethylamino)-4-pyridyl)vinyl]pyrazine and 2,3,5,6-tetrakis[2-((3-dimethylamino)-4-pyridyl)vinyl]pyrazine; those in which X is a nitro group such as 2,3,5,6-tetrakis[2-((3-nitro)-2-pyridyl)vinyl]pyrazine, 2,3,5,6-tetrakis[2-((4-nitro)-2-pyridyl)vinyl]pyrazine, 2,3,5,6-tetrakis[2-((5-nitro)-2-pyridyl)vinyl]pyrazine, 2,3,5,6-tetrakis[2-((6-nitro)-2-pyridyl)vinyl]pyrazine, 2,3,5,6-tetrakis[2-((2-nitro)-3-pyridyl)vinyl]pyrazine, 2,3,5,6-tetrakis[2-((4-nitro)-3-pyridyl)vinyl]pyrazine, 2,3,5,6-tetrakis[2-((5-nitro)-3-pyridyl)vinyl]pyrazine, 2,3,5,6-tetrakis[2-((6-nitro)-3-pyridyl)vinyl]pyrazine, 2,3,5,6-tetrakis[2-((2-nitro)-4-pyridyl)vinyl]pyrazine and 2,3,5,6-tetrakis[2-((3-nitro)-4-pyridyl)vinyl]pyrazine; those in which X is an acyloxy group such as 2,3,5,6-tetrakis [2-(4-benzoyloxyphenyl)vinyl]pyrazine; and those in which X is an acyloxycarbonyl group such as 2,3,5,6-tetrakis[2-(4-benzoyloxycarbonylphenyl)vinyl]pyrazine.

The tetravinylpyrazine compounds listed above can be prepared by reacting 2,3,5,6-tetramethyl pyrazine represented by the following chemical formula (2):

(2)

with aldehyde compounds represented by the following general formula (3):

X—R—CHO (3)

in the presence of an acid anhydride.

The acid anhydrides which may be used in the present invention include, for instance, benzoic anhydride, acetic anhydride and butyric anhydride, with benzoic anhydride being preferred. In addition, inorganic dehydrating agents such as zinc chloride may be used, but the use thereof is limited in the reaction rate or the like. Thus, the use of acid anhydrides is more preferred.

The reaction temperature ranges from 50° to 300° C., preferably 150° to 250° C. On the other hand, the reaction time varies depending on the reaction temperature selected, but in general ranges from several hours to 20 hours.

Regarding the atmosphere during the reaction, the reaction is preferably carried out while passing an inert gas such as nitrogen gas through the reaction system or having the reaction system filled with an inert gas in order to inhibit side reactions such as oxidation of starting compounds.

The reaction of tetramethyl pyrazine with the aldehyde compounds is preferably carried out in the presence of an excess of the aldehyde compounds and thus the molar ratio of the tetramethyl pyrazine to the aldehyde compound ranges from 1:1 to 1:20, preferably 1:5 to 1:15. In this respect, the relative ratio of the aldehyde compound to the acid anhydride is preferably approximately 1:1 expressed in terms of molar ratio.

The foregoing tetravinylpyrazine compounds of the present invention listed above are symmetrical compounds in which all of the four substituents represented by X-R- in Formula (1) are identical to one another, but it is also possible to prepare asymmetrical tetravinylpyrazine compounds in which a part or all of the four substituents are replaced with different substituents in the same manner discussed above. In this case, these four substituents can be introduced simultaneously or stepwise. If they are simultaneously introduced, the reaction rate of each aldehyde compound with tetravinylpyrazine is determined in advance and the charge rate of the aldehyde compounds is accordingly determined on the basis of the results. On the other hand, if they are stepwise introduced, these aldehyde compounds are reacted with tetramethyl pyrazine in such a manner that the aldehydes are introduced into the pyrazine in the order of increasing reaction rate to control the reaction time and hence the number of each substituent to be introduced. Thus, the asymmetrical tetravinylpyrazine compounds can be prepared.

The asymmetrical tetravinylpyrazine compounds obtained according to the foregoing method may be a mixture of different pyrazine compounds, but each component of the mixture can be isolated from other components by a variety of separation methods such as solvent separation, recrystallization and column separation.

A part or most of the compounds of Formula (1) in which the substituent X is a hydroxyl or carboxyl group prepared by the foregoing method in the presence of the acid anhydride are present in the form of esters or acid anhydrides, but they can easily be hydrolyzed to give the desired pyrazine compounds in which the substituent X is a hydroxyl or carboxyl group.

The tetravinylpyrazine compounds defined by Formula (1) are useful as materials for producing thin film light-emitting elements and non-linear optical elements.

Figure 2:
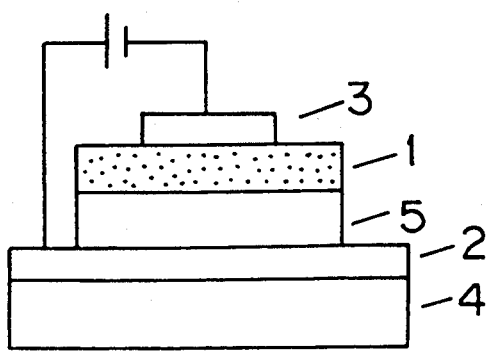
Figure 3:
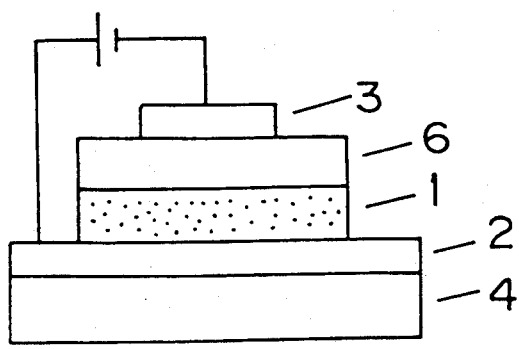

An important embodiment of the EL element according to the present invention has a structure which comprises, as a light-emitting source, at least one thin film comprising the tetravinylpyrazine compounds sandwiched between an electrode for injecting positive holes (hereinafter referred to as "first electrode") and an electrode for injecting electrons (hereinafter referred to as "second electrode"). More specifically, preferred embodiments have a monolayer or multilayer thin film structure comprising at least one light-emitting layer; a positive hole-transporting layer and light-emitting layer which are laminated in this order; or a positive hole-transporting layer, a light-emitting layer and an electron-transporting layer which are laminated in this order, the mono-or multi-layer thin film structure being positioned between these two electrodes. These preferred embodiments are shown in FIGS. 1 to 4. FIG. 1 shows an element comprising one layer of an organic thin film (1) comprising the tetravinylpyrazine compound. The organic thin film comprising the tetravinylpyrazine compound may comprise the tetravinylpyrazine compound alone or in combination with a positive hole-transporting material, an electron-transporting material or mixture thereof. FIG. 2 shows an element having a two-layer structure comprising a layer of an organic thin film (1) comprising the tetravinylpyrazine compound and a layer (5) of a positive hole-transporting material and FIG. 3 shows an element having a two-layer structure comprising a layer of an organic thin film (1) comprising the tetravinylpyrazine compound and a layer (6) of an electron-transporting material. In any case, the organic thin film layer may comprise the tetravinylpyrazine compound alone or in combination with a positive hole-transporting material, an electron-transporting material or mixture thereof.

Figure 4:
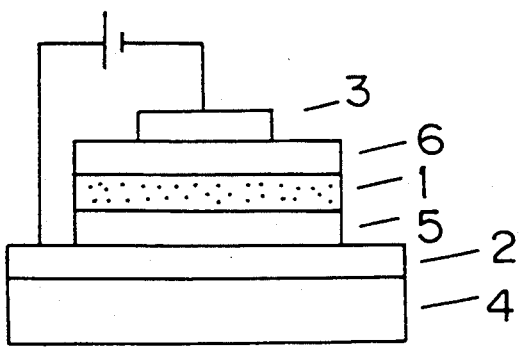

FIG. 4 shows an element having a three-layer structure which comprises a layer (5) of a positive hole-transporting material, a layer (1) of an organic thin film comprising the tetravinylpyrazine compound and a thin film layer (6) of an electron-transporting material. In this embodiment, the organic thin film layer may likewise comprise the tetravinylpyrazine compound alone or in combination with a positive-hole transporting material, an electron-transporting material or mixture thereof.

In FIGS. 1 to 4, the reference numeral (2) represents a first electrode of, for instance, a transparent conductive film; the reference numeral (3) is a second electrode such as a metal electrode and the reference numeral (4) is a substrate such as a glass substrate. The electrodes (2) and (3) are connected, respectively, to positive and negative terminals of a power supply.

The structure of these elements is not restricted to a specific one and is appropriately selected depending on the properties of the thin film comprising the tetravinylpyrazine compound.

The thin film comprising the tetravinylpyrazine compound can be formed from at least one compound represented by Formula (1). In short, it is important, in the present invention, to use a thin film comprising the tetravinylpyrazine compound.

These thin films can be formed according to a variety of methods such as vacuum deposition, sublimation and coating methods which are properly selected.

The thin film may have any structure such as an amorphous structure, a microcrystalline structure, a microcrystal-containing amorphous structure, a polycrystalline structure and a single crystal structure which are likewise appropriately selected. The preferred film-forming method is one which can provide a thin film free of pinholes and having a uniform thickness.

The thickness of the thin film is not restricted to a specific range, but is in general in the order of from 50 to 5000 Å. It is a matter of course that the thickness thereof may be beyond the range defined above.

The positive hole-transporting thin film will now be detailed below.

The positive hole-transporting film is a thin film of an organic or inorganic substance having an ability of transporting positive holes.

In the case of organic thin films, materials therefor are by no means limited to any specific ones and any known organic material having an ability of transporting positive holes may be used. Preferred examples thereof are diamine compounds such as N,N'-diphenyl-N,N'-bis-(3-methylphenyl)-1,1'-diphenyl-4,4'-diamine; phthalocyanine compounds such as copper phthalocyanine; polymeric compounds such as polyvinyl carbazole and polymethylphenyl silane.

The organic thin films may be formed by, for instance, vacuum deposition, sublimation and coating methods which are properly selected. In addition, it is also possible to use organic thin films prepared from a mixture of at least two such organic materials or by laminating at least two layers of one or more organic materials.

The thickness thereof is not restricted to a particular range, but usually ranges from 10 to 3000 Å. The thickness thereof may of course be beyond the range defined above.

The inorganic film may be a thin film of an amorphous or microcrystalline semiconductor. Preferred are, for instance, Si- and SiC-based materials, more preferably hydrogenated amorphous SiC, hydrogenated microcrystalline Si and hydrogenated microcrystalline SiC. The thin films of this type are made positive hole-conductive by modulation of the composition and doping and by laminating a plurality of thin films.

The thickness thereof is not likewise limited to a specific range, but in general ranges from 10 to 3000 Å. The thickness thereof may of course be beyond the range defined above.

These inorganic thin films can be prepared by a variety of thin film-foming techniques such as photo assisted CVD (chemical vapor deposition), plasma CVD, thermal CVD, MBE (molecular beam epitaxy), vapor deposition and sputtering methods.

Referring now to the electron-transporting thin films, these thin films are, for instance, organic and inorganic thin films having an ability of transporting electrons.

Materials for the organic thin films are not restricted to specific ones and may be any known organic materials having an ability of transporting electrons. Preferred examples thereof are metal complexes such as tris-(8-hydroxyquinolinol) aluminum; and oxadiazole compounds such as 2,5-bis-(4'-diethylamino-phenyl)-1,2,4-oxadiazole.

The electron-transporting organic thin films may be formed by, for instance, vacuum deposition, sublimation and coating methods which are properly selected. In addition, it is also possible to use organic thin films prepared from a mixture of at least two such organic materials or by laminating at least two layers of one or more organic materials.

The thickness thereof is not restricted to a particular range, but usually ranges from 10 to 3000 Å. The thickness thereof may of course be beyond the range defined above.

The electron-transporting inorganic thin films may be thin films of amorphous or microcrystalline semiconductors. Preferred are, for instance, Si- and SiC-based materials, more preferably hydrogenated amorphous SiC, hydrogenated microcrystalline Si and hydrogenated microcrystalline SiC. The thin films of this type are made electron-conductive by modulation of the composition thereof and doping and by laminating a plurality of thin films.

The thickness thereof is not likewise limited to a specific range, but in general ranges from 10 to 3000 Å. The thickness thereof may of course be beyond the range defined above.

These inorganic thin films can be prepared by a variety of thin film-foming techniques such as photo assisted CVD, plasma CVD, thermal CVD, MBE, vapor deposition and sputtering methods.

The first electrode will now be explained in detail below.

The first electrode can be formed from thin films of, for instance, metals, alloys, metal oxides and metal silisides; thin films of, for instance, conductive polymers; and laminated thin films of these materials. Preferred examples thereof include transparent conductive films of; for instance, tin oxide ($SnO_2$), indium tin oxide (ITO) and zinc oxide (ZnO); metal films such as gold (Au); and conductive polymers such as polyarylene vinylene and polythiophene.

The second electrode will now be explained in detail below.

The second electrode can be formed from thin films of, for instance, metals, alloys, metal oxides and metal silisides and laminated thin films of these materials. Preferred are metal thin films of Group II of the Periodic Table such as Mg and Group III such as Al; metal alloy thin films of Groups II and I such as Mg-Ag; and metal alloy thin films of Groups II and III such as Mg-In.

The thickness of the foregoing electrodes are not restricted to a specific range, but in general range from 10 to 5000 Å. The thickness thereof may of course be beyond the range defined above.

The foregoing electrodes can be prepared according to a variety of thin film-forming methods such as vapor deposition, sputtering, electrolytic polymerization and coating methods which are properly selected.

The method for producing the EL element of the present invention and for evaluating the resulting element will hereinafter be explained in detail.

A transparent conductive film is first applied onto the surface of a glass substrate through the electron beam vacuum deposition technique. A positive hole-transporting material, a light-emitting material and an electron-transporting material (several mg each) are charged into a plurality of quartz boats (1 cc volume) which are wound with-heating wires (1 $\phi$; 5 turns). These quartz boats are heated by passing an electric current (8 Å) through the heating wires under vacuum to deposit the materials. In this respect, however, if thin films having different properties are laminated, an electric current is in order-passed through each corresponding boat to deposit the material. In addition, if a mixed film of the materials having different properties is deposited, the materials are co-deposited by simultaneously passing an electric current through a desired number of quartz boats while monitoring the deposition rate to determine the mixing ratio of the materials.

The deposition is performed at a degree of vacuum in the order of 5E-5 (Torr). The film thickness is monitored using a quartz oscillator. The film thickness is determined by the correlative data prepared in advance between the number of vibration and the film thickness. The substrate carrying a deposited film is taken out of the vacuum chamber and placed on a metal mask of another vacuum deposition system so that a part thereof is not covered with a metal layer. Then metal particles are placed on a coiled tungsten wire (0.5 φ; 4 turns), the vaccum chamber is evacuated to a degree of vacuum of about 2E-6 (Torr) and then an electric current of about 12 Å is passed through the tungsten wire to deposit the metal. The deposited substrate is taken out of the vacuum chamber and the transparent electrode and the metal electrode are connected, respectively, to the positive and negative voltage terminals of a DC power supply. The volume of the DC power supply is gradually increased while observing the voltage, electric current and brightness of the emitted light by measuring apparatuses.

The present invention also relates to a non-linear optical material which makes use of the tetravinylpyrazine compound of the invention.

The non-linear optical devices make use of the tertiary non-linear optical effect and examples thereof include optical bistable elements and optical gate switches. Therefore, the non-linear optical materials used for producing these devices must be those exhibiting tertiary non-linear optical effects.

The inventors of this invention have conducted intensive studies, have found that specific tetravinylpyrazine compounds show high tertiary non-linear optical effects and thus have completed the present invention.

The tetravinylpyrazine compounds have molecular structures having two-dimensional $\pi$ electron conjugated systems which are effective for obtaining high non-linear optical effects.

The non-linear optical materials according to the present invention comprise a tetravinylpyrazine compound represented by Formula (1). In this case, the tetravinylpyrazine compound can be used alone or in combination with other organic or inorganic materials. The compounds may be in amorphous states, microcrystalline states, microcrystal-containing amorphous states or polycrystalline states which may be appropriately selected. Preferred are those comprising regularly arranged molecules from the optical standpoint.

The non-linear optical material is preferably in the form which comprises a substrate provided thereon with a thin film of the tetravinylpyrazine compound; or a thin layer or a film of the compound dispersed in another organic material such as a polymer; or such a layer or film deposited on a substrate. The thickness of the optical material is on the order of 10 Å to 100 μ. The non-linear optical material can be formed by a variety of methods such as vapor deposition, sublimation and coating methods which are appropriately selected.

If the compounds of the present invention are used for the production of electroluminescent elements and non-linear optical material, the substituent X in Formula (1) is preferably a hydrogen atom, an alkyl group, a halogen atom, a phenyl group, a dialkylamino group or an alkoxy group.

The present invention will hereinafter be described in more detail with reference to the following non-limitative working Examples.

Example 1

To a 200 ml volume egg-plant type flask equipped with a reflux condenser and a tube for introducing nitrogen gas, there were added 3.00 g (0.022 mole) of 2,3,5,6-tetramethyl pyrazine, 28.05 g (0.264 mole) of benzaldehyde and 59.72 g (0.264 mole) of benzoic anhydride and the contents of the flask were reacted for 10 hours with heating at 230° C. in a silicone oil bath while gradually passing nitrogen gas. After the reaction, the heating was interrupted, 100 ml of ethanol was added when the temperature of the reaction system reached 60° to 65° and the system was allowed to stand overnight. Crystals precipitated were recovered through filtration under reduced pressure. The crystals recovered on a filters paper were washed several times with ethanol and dried under reduced pressure. After drying, the crystals were recrystallized from toluene to give 2,3,5,6-tetrakis[2-(phenyl)vinyl]pyrazine as needles of pale yellowish brown. The yield thereof was 5.19 g (48.3%).

Figure 5A:
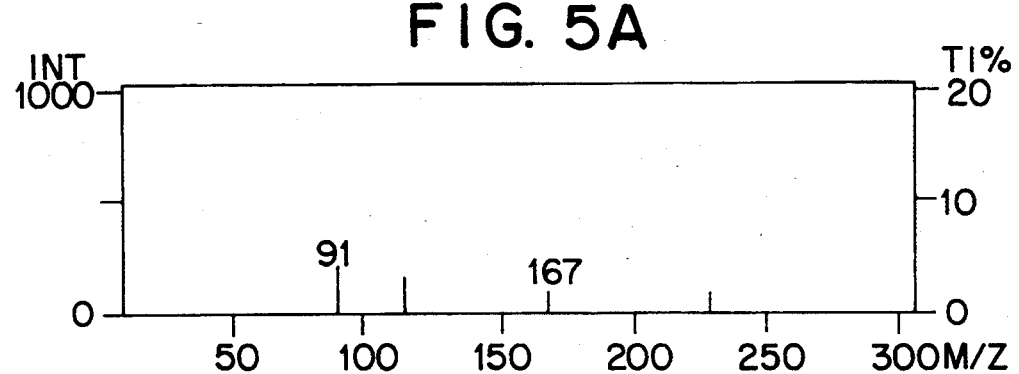
FIG. 5 is a mass spectrogram of the compound of the present invention obtained in Example 1.
Figure 5B:
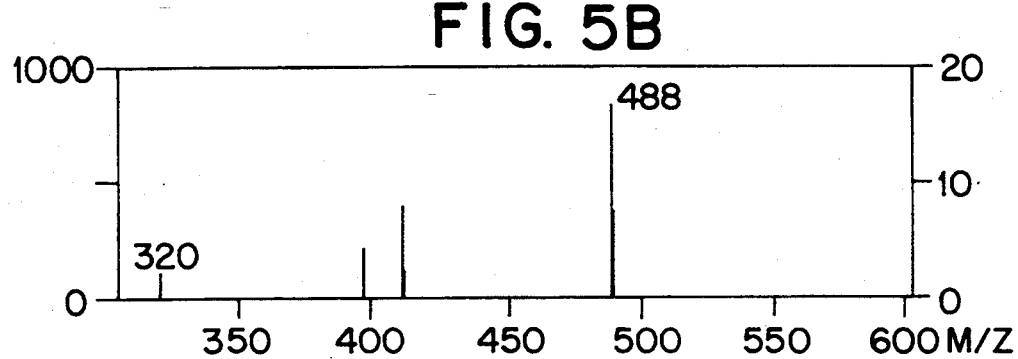
Figure 6:
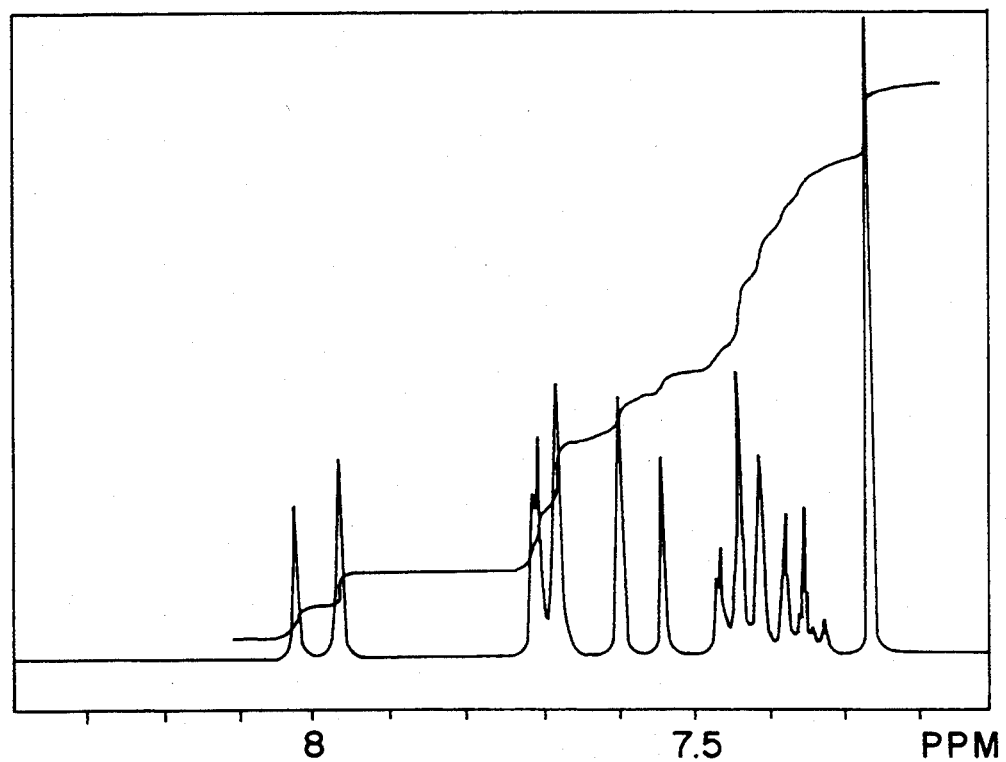
FIG. 6 is an $^1$H-NMR spectrogram of the compound of the present invention obtained in Example 1.

The melting point of the resulting 2,3,5,6-tetrakis[2-(phenyl)vinyl]pyrazine was 261.5°–263.5° C. The mass spectrogram and NMR spectrogram of the product are shown in FIGS. 5 and 6 respectively.

Example 2

To a 200 ml volume egg-plant type flask equipped with a reflux condenser and a tube for introducing nitrogen gas, there were added 2.00 g (0.0147 mole) of 2,3,5,6-tetramethyl pyrazine, 21.17 g (0.176 mole) of 4-methylbenzaldehyde and 39.88 g (0.176 mole) of benzoic anhydride and the contents of the flask were reacted for 10 hours with heating at 240° C. in a silicone oil bath while gradually passing nitrogen gas. After completion of the reaction, the heating was interrupted, 100 ml of ethanol was added when the temperature of the reaction system reached 60° to 65° C. and the system was allowed to stand overnight.

Crystals precipitated were recovered through filtration under reduced pressure. The crystals recovered on a filter paper were washed several times with ethanol and dried under reduced pressure. After drying, the crystals were recrystallized from toluene to give 2,3,5,6-tetrakis[2-(4-methylphenyl) vinyl]pyrazine as needles of golden yellow. The yield thereof was 5.19 g (48.3%).

Figure 7A:
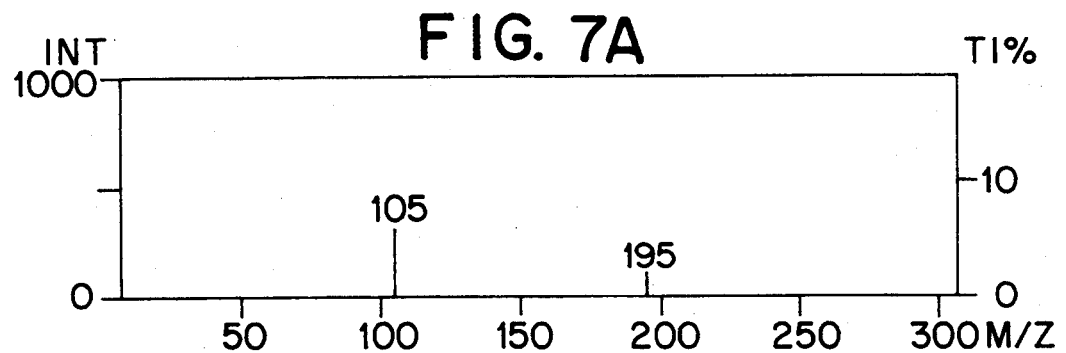
FIG. 7 is a mass spectrogram of the compound of the present invention obtained in Example 2.
Figure 7B:
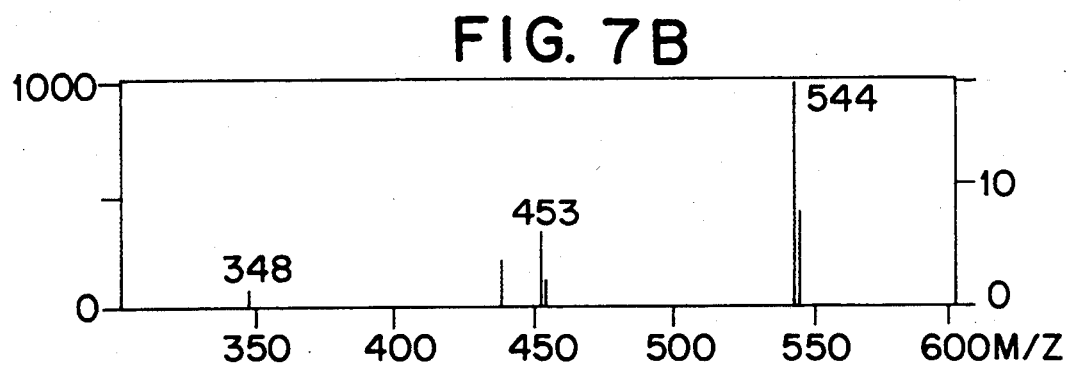
Figure 8:
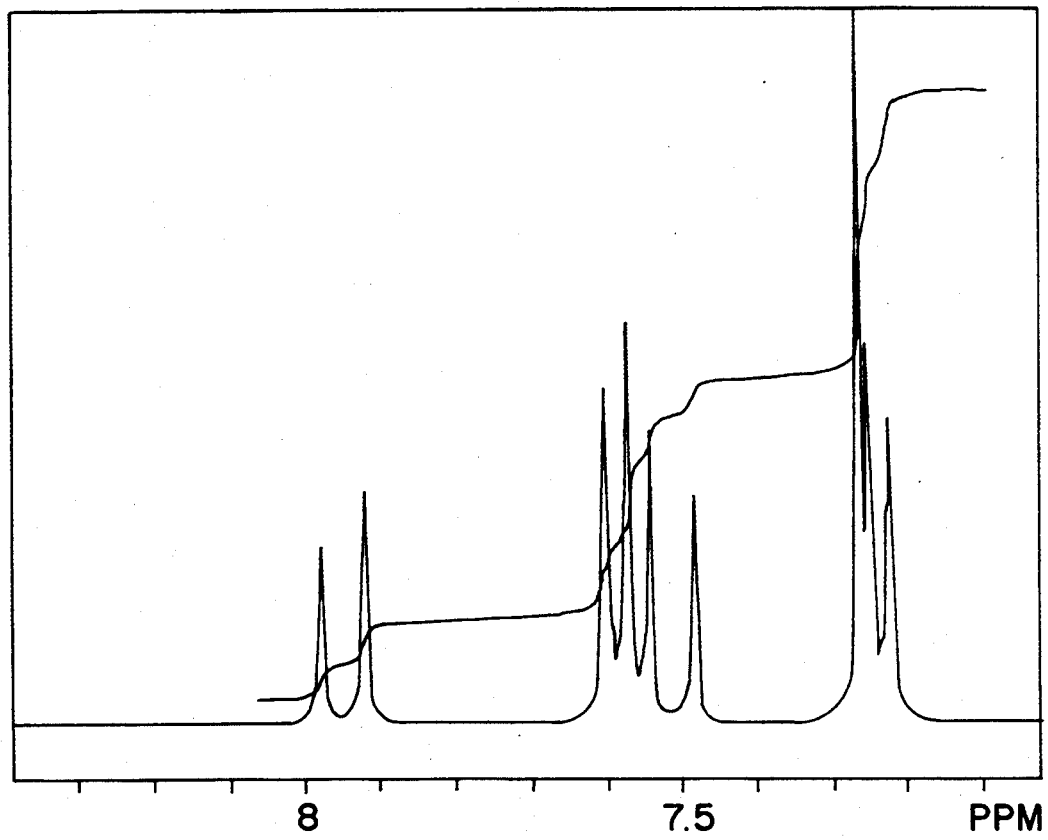
FIG. 8 is an $^1$H-NMR spectrogram of the compound of the present invention obtained in Example 2.

The melting point of the resulting 2,3,5,6-tetrakis[2-(4-methylphenyl)vinyl]pyrazine was 283°–286° C. The mass spectrogram and NMR spectrogram thereof are shown in FIGS. 7 and 8 respectively.

Example 3

To a 200 ml volume egg-plant type flask equipped with a reflux condenser and a tube for introducing nitrogen gas, there were added 2.00 g (0.0147 mole) of 2,3,5,6-tetramethyl pyrazine, 24.74 g (0,176 mole) of 4-chlorobenzaldehyde and 39.88 g (0.176 mole) of benzoic anhydride and the contents of the flask were reacted for 10 hours with heating at 240° C. in a silicone oil bath while gradually passing nitrogen gas. After completion of the reaction, the heating was interrupted, 100 ml of ethanol was added when the temperature of the reaction system reached 60° to 65° C. and the system was allowed to stand overnight.

Crystals precipitated were recovered through filtration under reduced pressure. The crystals recovered on a filter paper were washed several times with ethanol and dried under reduced pressure. After drying, the crystals were recrystallized from toluene to give 2,3,5,6-tetrakis[2-(4-chlorophenyl) vinyl]pyrazine as needles of orange color. The yield thereof was 5.83 g (63.3%).

Figure 9A:
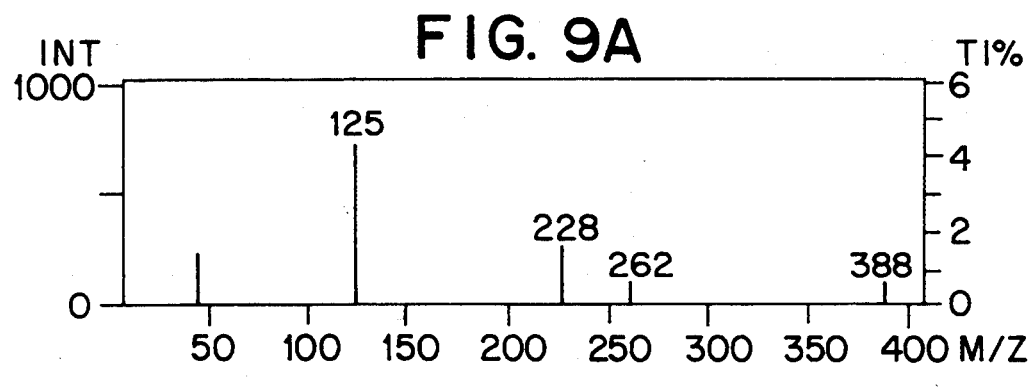
FIG. 9 is a mass spectrogram of the compound of the present invention obtained in Example 3.
Figure 9B:
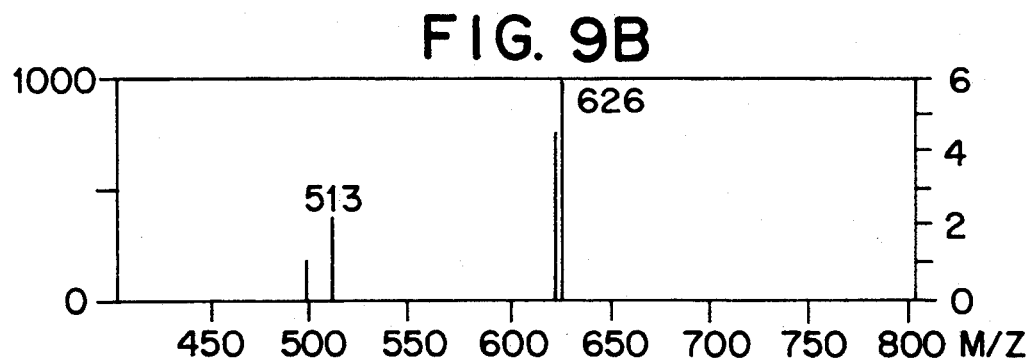
Figure 10:
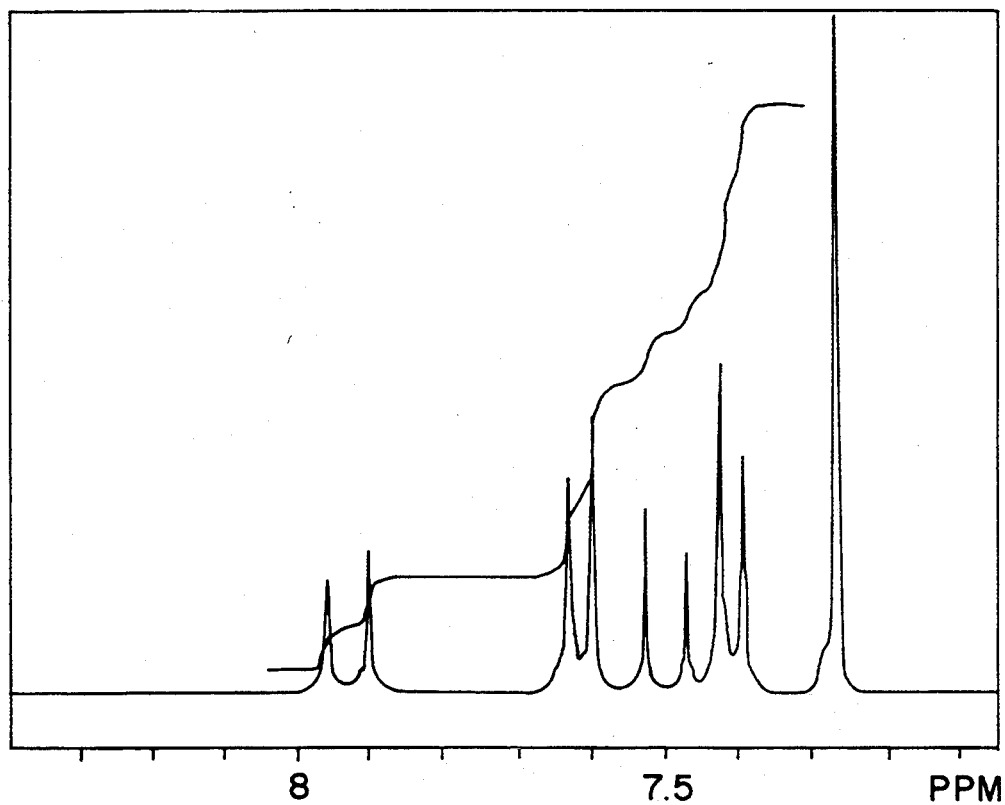
FIG. 10 is an $^1$H-NMR spectrogram of the compound of the present invention obtained in Example 3.

The melting point of the resulting 2,3,5,6-tetrakis[2-(4chlorophenyl)vinyl]pyrazine was 317°–318° C. The mass spectrogram and NMR spectrogram thereof are shown in FIGS. 9 and 10 respectively.

Example 4

To a 200 ml volume egg-plant type flask equipped with a reflux condenser and a tube for introducing nitrogen gas, there were added 2.00 g (0.0147 mole) of 2,3,5,6-tetramethyl pyrazine, 27.53 g (0.176 mole) of 1-naphthylaldehyde and 39.88 g (0.176 mole) of benzoic anhydride and the contents of the flask were reacted for 9 hours with heating at 230° C. in a silicone oil bath while gradually passing nitrogen gas. After completion of the reaction, the heating was interrupted, 100 ml of ethanol was added when the temperature of the reaction system reached 60° to 65° C. and the system was allowed to stand overnight.

Crystals precipitated were recovered through filtration under reduced pressure. The crystals recovered on a filter paper were washed several times with ethanol and dried under reduced pressure. After drying, the crystals were recrystallized from toluene to give 2,3,5,6-tetrakis[2-(1-naphthyl)vinyl]pyrazine as red needles. The yield thereof was 0.21 g (2.1%).

Figure 11A:
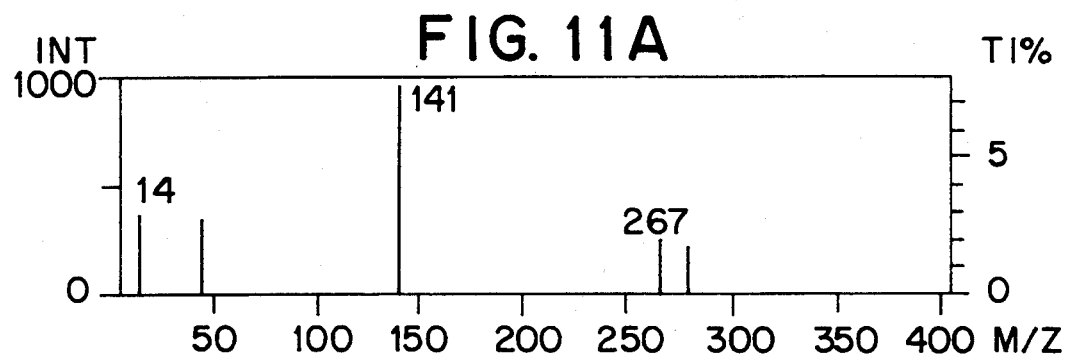
FIG. 11 is a mass spectrogram of the compound of the present invention obtained in Example 4.
Figure 11B:
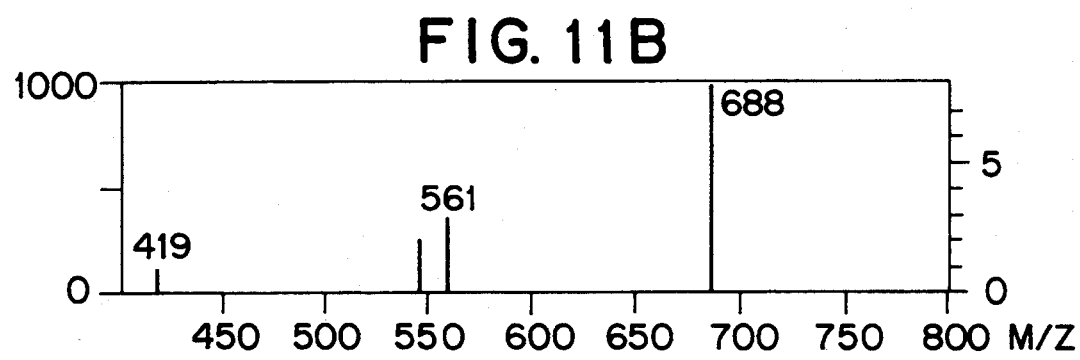
Figure 12:
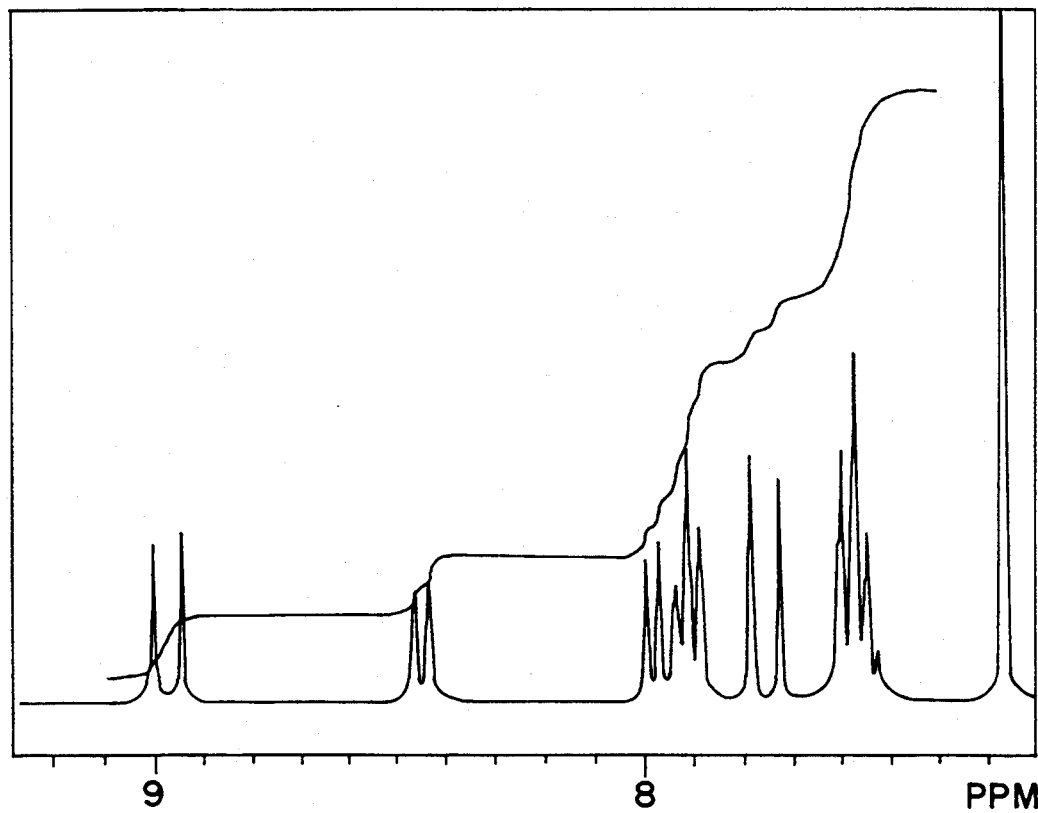
FIG. 12 is an $^1$H-NMR spectrogram of the compound of the present invention obtained in Example 4.

The melting point of the resulting 2,3,5,6-tetrakis [2-(1-naphthyl)vinyl]pyrazine was 311°–315° C. The mass spectrogram and NMR spectrogram thereof are shown in FIGS. 11 and 12 respectively.

Example 5

To a 300 ml volume flask equipped with a reflux condenser and a tube for introducing nitrogen gas, there were added 3.00 g (0,022 mole) of 2,3,5,6-tetramethyl pyrazine, 28.31 g (0.264 mole) of pyridine-3-aldehyde and 41.76 g (0.264 mole) of butyric anhydride and the contents of the flask were heated for 7 hours at 230° C. while passing nitrogen gas. After completion of the reaction and cooling down to about room temperature, an aqueous solution of sodium hydroxide (25.34 g NaOH/100 ml H₂O) was added and the mixture was stirred. To the mixture, there was added 130 ml of methylene chloride, followed by stirring and allowing to stand overnight. Since solids were precipitated out in the methylene chloride phase, the solids were filtered after removing the water phase.

The solids were dried and then recrystallized from dimethylformamide (DMF) to give 4.34 g (yield 40.11%) of 2,3,5,6-tetrakis[2-(3-pyridyl)vinyl]pyrazine as needles of orange color.

The melting point of the resulting 2,3,5,6-tetrakis[2-(3-pyridyl)vinyl]pyrazine was 300°–302° C. The resulting crystal was confirmed to be the desired compound by mass spectroscopic and NMR spectroscopic measurements.

Example 6

To a 500 ml volume flask equipped with a reflux condenser and a tube for introducing nitrogen gas, there were added 3.00 g (0.022 mole) of 2,3,5,6-tetramethyl pyrazine, 32.24 g (0.264 mole) of p-hydroxybenzaldehyde, 59.80 g (0.264 mole) of benzoic anhydride and 100 ml of decalin and the contents of the flask were refluxed for 7 hours while passing nitrogen gas. After completion of the reaction and cooling down to about 50 ° C., 200 ml of ethanol was added and the mixture was allowed to stand overnight.

The solids precipitated were dried and then recrystallized from DMF-ethanol mixed solvent to give 11.28 g (yield 52.96%) of 2,3,5,6-tetrakis[2-(4-benzoyloxyphenyl)vinyl]pyrazine as yellow needles.

The melting point of the resulting 2,3,5,6-tetrakis[2-(4-benzoyloxyphenyl)vinyl]pyrazine was 249°–251° C. The resulting crystal was confirmed to be the intended compound by mass spectroscopic and NMR spectroscopic measurements.

Example 7

To a 200 ml volume flask equipped with a reflux condenser, there was added 2.13 g (0.022 mole) of 2,3,5,6-tetrakis[2-(4-benzoyloxyphenyl)vinyl]pyrazine and then 30 ml of DMF was added to dissolve the compound. A 3% sodium hydroxide solution (141 ml) was added to the flask and the contents of the flask were reacted by heating at 90° C. for one hour. After completion of the reaction and cooling down to about room temperature, 100 ml of acetone was added and the mixture was sufficiently stirred.

The solids formed were filtered off and the filtrate was concentrated. Methanol was added to the concentrate to give solids. The solids were dissolved under heating and recrystallized from the methanol to give 2,3,5,6-tetrakis[2-(4-hydroxyphenyl)vinyl]pyrazine as yellow crystals.

The resulting crystal was confirmed to be the intended compound by mass spectroscopic and NMR spectroscopic measurements.

Example 8

To a 500 ml volume flask equipped with a reflux condenser and a tube for introducing nitrogen gas, there were added 3.00 g (0,022 mole) of 2,3,5,6-tetramethyl pyrazine, 39.63 g (0.264 mole) of p-formylbenzoic acid, 59.80 g (0,264 mole) of benzoic anhydride and 150 ml of decalin and the contents of the flask were refluxed for 5 hours while passing nitrogen gas. After completion of the reaction, the reaction system was allowed to stand overnight to give yellow solids. An amount of 200 ml of ethanol was added and the mixture was stirred for 2 hours.

The solids precipitated were filtered and then dried to give 30.63 g of 2,3,5,6-tetrakis[2-(4-benzoyloxycarbonylphenyl) vinyl]pyrazine as yellow solids.

The resulting solids were confirmed to be the intended compound by mass spectroscopic and NMR spectroscopic measurements.

Example 9

An ITO film of 1000 Å thickness serving as a first electrode was formed on a glass substrate. As a positive hole-transporting thin film, a film of N,N'-diphenyl-N,N'-bis-(3-methylphenyl)-1,1'-diphenyl-4,4'-diamine was formed to a thickness of 600 Å by the resistance heating evaporation method. As a light-emitting layer, an organic thin film of 2,3,5,6-tetrakis[2-(phenyl)vinyl]pyrazine was formed to a thickness of 600 Å by the resistance heating evaporation method. Further an Mg metal layer was deposited by the resistance heating evaporation method to give a second electrode and to thus complete an EL element having a structure as shown in FIG. 2. In this respect, the area of the deposited film of Mg metal was 1 cm square. The ITO electrode and the Mg electrode were, respectively, connected to positive and negative voltage terminals of a power supply and an electric voltage was applied to the element. As a result, a bright yellow light which could be recognized under the irradiation with light rays from an indoor fluorescent lamp was emitted from the element at a voltage of not less than ten-odd volts. More specifically, the brightness observed was 1100 (cd/m$^2$) at an applied DC voltage of 13 V and a current density of 56 mA/cm$^2$. Moreover, the EL element emitted a light at high brightness and showed stable properties. More specifically, it was confirmed that the element could withstand continuous operation over several thousand hours at a brightness of several hundreds (cd/m$^2$).

Example 10

An ITO film of 1000 Å thickness serving as a first electrode was formed on a glass substrate. As a positive hole-transporting thin film, a film of N,N'-diphenyl-N,N'-bis-(3-methylphenyl)-1,1'-diphenyl-4,4'-diamine was formed to a thickness of 600 Å by the resistance heating evaporation method. As a light-emitting layer, an organic thin film of 2,3,5,6-tetrakis[2-(phenyl)vinyl]-pyrazine was formed to a thickness of 300 Å by the resistance heating evaporation method. Then a thin film of tris-(8-hydroxyquinolinol)aluminum serving as an electron-transporting thin film was formed on the light-emitting film to a thickness of 300 Å by the resistance heating evaporation method. Further an Mg metal thin film was deposited by the resistance heating evaporation method to give a second electrode and to thus complete an EL element having a structure as shown in FIG. 4. In this respect, the area of the deposited film of Mg metal was 1 cm square. The ITO electrode and the Mg electrode were, respectively, connected to positive and negative voltage terminals of a power supply and an electric voltage was applied to the element. As a result, a bright yellow light which could be recognized under the irradiation with light rays from an indoor fluorescent lamp was emitted from the element at a voltage of not less than ten-odd volts. More specifically, the brightness observed was 3357 (cd/m$^2$) at an applied DC voltage of 28 V and a current density of 156 mA/cm$^2$. Moreover, the EL element emitted a light at high brightness and showed stable properties. More specifically, it was confirmed that the element could withstand continuous operation over several thousand hours at a brightness of several hundreds (cd/m$^2$).

Example 11

An ITO film of 1000 Å thickness serving as a first electrode was formed on a glass substrate. As a positive hole-transporting thin film, a film of N,N'-diphenyl-N,N'-bis-(3-methylphenyl)-1,1'-diphenyl-4,4'-diamine was formed to a thickness of 600 Å by the resistance heating evaporation method. As a light-emitting layer, an organic thin film of 2,3,5,6-tetrakis[2-(4-methylphenyl)vinyl]pyrazine was formed to a thickness of 300 Å by the resistance heating evaporation method. Then a thin film of tris-(8-hydroxyquinolinol)aluminum serving as an electron-transporting thin film was formed on the light-emitting film to a thickness of 300 Å by the resistance heating evaporation method. Further an Mg metal thin film was deposited by the resistance heating evaporation method to give a second electrode and to thus complete an EL element having a structure as shown in FIG. 4. In this respect, the area of the deposited film of Mg metal was 1 cm square. The ITO electrode and the Mg electrode were, respectively, connected to positive and negative voltage terminals of a power supply and an electric voltage was applied to the element. As a result, a bright yellow light which could be recognized under the irradiation with light rays from an indoor fluorescent lamp was emitted from the element at a voltage of not less than ten-odd volts. More specifically, the brightness observed was 4069 (cd/m$^2$) at an applied DC voltage of 32 V and a current density of 151 mA/cm$^2$. Moreover, the EL element emitted a light at high brightness and showed stable properties. More specifically, it was confirmed that the element could withstand continuous operation over several thousand hours at a brightness several hundreds (cd/m$^2$).

Example 12

An ITO film of 1000 Å thickness serving as a first electrode was formed on a glass substrate. As a positive hole-transporting thin film, a film of N,N'-diphenyl-N,N'-bis-(3-methylphenyl)-1,1'-diphenyl-4,4'-diamine was formed to a thickness of 600 Å by the resistance heating evaporation method. As a light-emitting layer, an organic thin film of 2,3,5,6-tetrakis[2-(4-chlorophenyl)vinyl]pyrazine was formed to a thickness of 300 Å by the resistance heating evaporation method. Then a thin film of tris-(8-hydroxyquinolinol)aluminum serving as an electron-transporting thin film was formed on the light-emitting film to a thickness of 300 Å by the resistance heating evaporation method. Further an Mg metal thin film was deposited by the resistance heating evaporation method to give a second electrode and to thus complete an EL element having a structure as shown in FIG. 4. In this respect, the area of the deposited film of Mg metal was 1 cm square. The ITO electrode and the Mg electrode were, respectively, connected to positive and negative voltage terminals of a power supply and an electric voltage was applied to the element. As a result, a bright yellow light which could be recognized under the irradiation with light rays from an indoor fluorescent lamp was emitted from the element at a voltage of not less than ten-odd volts. More specifically, the brightness observed was 1513 (cd/m$^2$) at an applied DC voltage of 35 V and a current density of 75 mA/cm$^2$. Moreover, the EL element emitted a light at high brightness and showed stable properties. More specifically, it was confirmed that the element could withstand continuous operation over several thousand hours at a brightness of several hundreds (cd/m$^2$).

Example 13

An ITO film of 1000 Å thickness serving as a first electrode was formed on a glass substrate. As a positive hole-transporting thin film, a film of N,N'-diphenyl-N,N'-bis-(3-methylphenyl)-1,1'-diphenyl-4,4'-diamine was formed to a thickness of 600 Å by the resistance heating evaporation method. As a light-emitting layer, an organic thin film of 2,3,5,6-tetrakis[2-(1-naphthyl)-vinyl]pyrazine was formed to a thickness of 300Å by the resistance heating evaporation method. Then a thin film of tris-(8-hydroxyquinolinol)aluminum serving as an electron-transporting thin film was formed on the light-emitting film to a thickness of 300 Å by the resistance heating evaporation method. Further an Mg metal thin film was deposited by the resistance heating evaporation method to give a second electrode and to thus complete an EL element having a structure as shown in FIG. 4. In this respect, the area of the deposited film of Mg metal was 1 cm square. The ITO electrode and the Mg electrode were, respectively, connected to positive and negative voltage terminals of a power supply and an electric voltage was applied to the element. As a result, a bright yellow light which could be recognized under the irradiation with light rays from an indoor fluorescent lamp was emitted from the element at a voltage of not less than ten-odd volts. More specifically, the brightness observed was 752 (cd/m$^2$) at an applied DC voltage of 29 V and a current density of 80 mA/cm$^2$. Moreover, the EL element emitted a light at high brightness and showed stable properties. More specifically, it was confirmed that the element could withstand continuous operation over several thousand hours at a brightness of several hundreds (cd/m$^2$).

Example 14

An ITO film of 1000 Å thickness serving as a first electrode was formed on a glass substrate. As a positive hole-transporting thin film, a film of N,N'-diphenyl-N,N'-bis-(3-methylphenyl)-1,1'-diphenyl-4,4'-diamine was formed to a thickness of 600 Å by the resistance heating evaporation method. As a light-emitting layer, an organic thin ,film of 2,3,5,6-tetrakis[2-(3-pyridyl)-vinyl]pyrazine was formed to a thickness of 600 Å by the resistance heating evaporation method. Further an Mg metal thin film was deposited by the resistance heating evaporation method to give a second electrode and to thus complete an EL element having a structure as shown in FIG. 2. In this respect, the area of the deposited film of Mg metal was 1 cm square. The ITO electrode and the Mg electrode were, respectively, connected to positive and negative voltage terminals of a power supply and an electric voltage was applied to the element. As a result, a bright orange light which could be recognized under the irradiation with light rays from an indoor fluorescent lamp was emitted from the element at a voltage of not less than ten-odd volts. More specifically, the brightness observed was 250 (cd/m$^2$) at an applied DC voltage of 24 V and a current density of 77 mA/cm$^2$. Moreover, the EL element emitted a light at high brightness and showed stable properties. More specifically, it was confirmed that the element could withstand continuous operation over several thousand hours at a brightness of several hundreds (cd/m$^2$).

Example 15

An ITO film of 1000 Å thickness serving as a first electrode was formed on a glass substrate. As a positive hole-transporting thin film, a film of N,N'-diphenyl-N,N'-bis-(3-methylphenyl)-1,1'-diphenyl-4,4'-diamine was formed to a thickness of 600 Å by the resistance heating evaporation method. As a light-emitting layer, an organic thin film of 2,3,5,6-tetrakis[2-(3-pyridyl)-vinyl]pyrazine was formed to a thickness of 300 Å by the resistance heating evaporation method. Then a thin film of tris-(8-hydroxyquinolinol)aluminum serving as an electron-transporting thin film was formed on the light-emitting film to a thickness of 300 Å by the resistance heating evaporation method. Further an Mg metal thin film was deposited by the resistance heating evaporation method to give a second electrode and to thus complete an EL element having a structure as shown in FIG. 4. In this respect, the area of the deposited film of Mg metal was 1 cm square. The ITO electrode and the Mg electrode were, respectively, connected to positive and negative voltage terminals of a power supply and an electric voltage was applied to the element. As a result, a bright orange light which could be recognized under the irradiation with light rays from an indoor fluorescent lamp was emitted from the element at a voltage of not less than ten-odd volts. More specifically, the brightness observed was 120 (cd/m$^2$) at an applied DC voltage of 23 V and a current density of 21 mA/cm$^2$. Moreover, the EL element emitted a light at high brightness and showed stable properties. More specifically, it was confirmed that the element could withstand continuous operation over several thousand hours at a brightness of several hundreds (cd/m$^2$).

The present invention can provide electroluminescent elements which comprise thin films of uniform thickness, have excellent light-emitting properties and thermal stability and can withstand the operation over a long time, as seen from the results obtained in Examples 9 to 15.

Example 16

An organic thin film of 2,3,5,6-tetrakis[2-(phenyl)vinyl]pyrazine was deposited onto a quartz substrate to a thickness of 500 Å by the resistance heating evaporation method. The value of $\chi^{(3)}$ of the organic thin film was determined by the four-light wave mixing method and found to be $1.39 \times 10^{-6}$ esu at 460 nm. This value is two digits higher than those of the conventionally known organic non-linear optical materials.

Example 17

An organic thin film of 2,3,5,6-tetrakis[2-(4-methylphenyl)vinyl]pyrazine was deposited onto a quartz substrate to a thickness of 500 Å by the resistance heating evaporation method. The value of $\chi^{(3)}$ of the organic thin film was determined by the four-light wave mixing method and found to be $2.65 \times 10^{31\ 6}$ esu at 460 nm. This value is two digits higher than those of the conventionally known organic nonlinear optical materials.

Example 18

An organic thin film of 2,3,5,6-tetrakis[2-(4-chlorophenyl)vinyl]pyrazine was deposited onto a quartz substrate to a thickness of 500 Å by the resistance heating evaporation method. The value of $\chi^{(3)}$ of the organic thin film was determined by the four-light wave mixing method and found to be $1.03 \times 10^{-6}$ esu at 460 nm. This value is two digits higher than those of the conventionally known organic nonlinear optical materials.

Example 19

An organic thin film of 2,3,5,6-tetrakis[2-(1-naphthyl)vinyl]pyrazine was deposited onto a quartz substrate to a thickness of 500 Å by the resistance heating evaporation method. The value of $\chi^{(3)}$ of the organic thin film was determined by the four-light wave mixing method and found to be $1.25 \times 10^6$ esu at 460 nm. This value is two digits higher than those of the conventionally known organic non-linear optical materials.

Example 20

Figure 13:
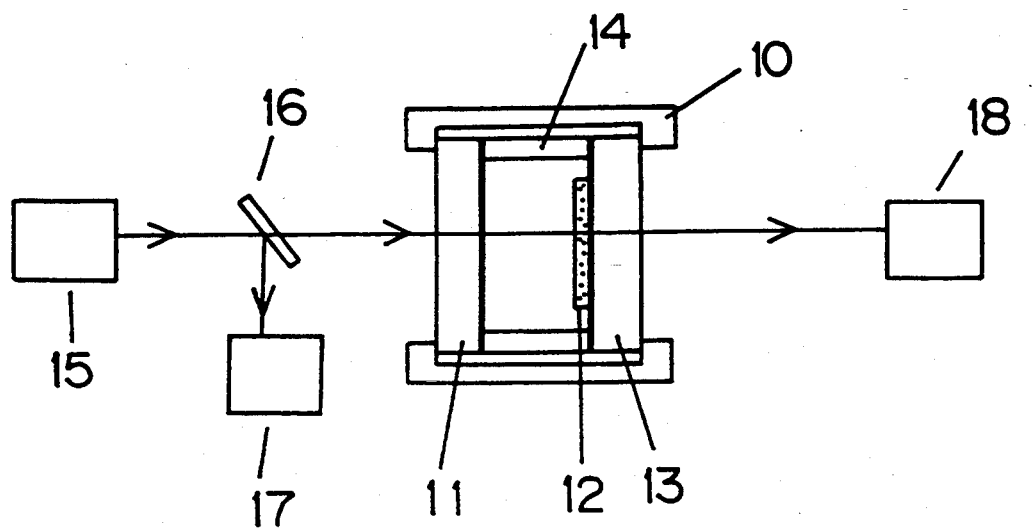
FIG. 13 is a schematic diagram showing an optical bistable element obtained using the non-linear optical material of the present invention and an apparatus for evaluating the quality of the optical bistable element.
Figure 14:
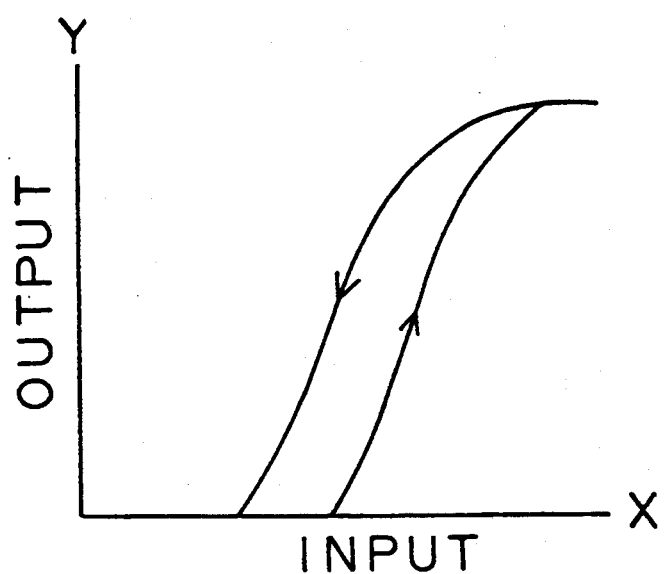
FIG. 14 is a graph showing the quality of the non-linear optical material according to the present invention.

An optical bistable element was produced as an example of a tertiary non-linear optical device. The structure of the resulting optical bistable element and an apparatus for evaluating properties thereof are shown in FIG. 13. As shown in FIG. 13, a film of 2,3,5,6-tetrakis[2-(phenyl)vinyl]pyrazine vapor-deposited on a glass plate 13 through an anti-reflection coating and a glass plate 11 provided with an anti-reflection coating were held by a metal holder through spacers 14 of PZT to give a Fabry-Perot type element. The light rays from a variable-wavelength laser source 15 was divided into two portions through a half mirror 16 and one of these was guided towards a Fabry-Perot type element. The light rays passed through the etalon were detected by a photodetector 18. The laser rays used had a wavelength of 460 nm and were focused on the etalon at an intensity of 100 mW to give a spot of 10 μm. The resulting data were displayed and plotted on an oscilloscope with the intensity of light incident upon the etalon on the X-axis and that of light passing through the etalon on the Y-axis, while changing the intensity of the light incident upon the etalon. As a result, when the intensity of the incident light was first increased and then decreased, the intensity of the output light followed two different traces as shown in FIG. 14, i.e., exhibited the bistable characteristic. The device exhibited this characteristic even at a light intensity of not more than 10 mW. Thus the non-linear optical material according to the present invention shows excellent quality.

The results obtained in the foregoing Examples 16 to 20 clearly indicate that the non-linear optical material which makes use of the tetravinylpyrazine compound exhibits the nonlinear optical effect substantially greater than that achieved by the conventional materials.

We claim:

1. A tetravinylpyrazine compound having electroluminescence represented by the following formula (1):

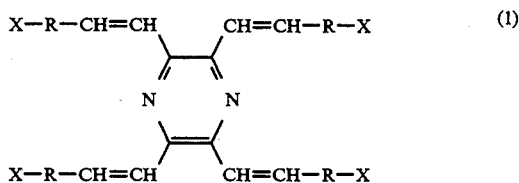

wherein R represents a [benzene, naphthalene, anthracene, pyrene, pyridine, quinoline, furan, thiophene, benzoxazole or benzothiazole]divalent phenylene, naphthylene, anthrylene, pyrenylene, pyridinylene, quinolinylene, furanylene, thiophenylene, benzathiazolylene or benzothiazolylene ring; X represents a hydrogen atom, a methyl, ethyl or propyl group, a cyclopentyl or cyclohexyl group, a phenyl or naphthyl group, a halogen atom, a hydroxyl group, a methoxy or ethoxy group, a carboxyl group, a methoxycarbonyl or ethoxycarbonyl group, an acetylamino group, a dimethylamino or diethylamino group, a nitro group, a benzoyloxy group or a benzoyloxycarbonyl group.

2. The tetravinylpyrazine compound of claim 1 wherein, in the formula (1), the substituent X is a hydrogen atom, a methyl, ethyl or propyl group, a halogen atom, a phenyl group, a dimethylamino group, a diethylamino group, a methoxy group or an ethoxy group.

3. The tetravinylpyrazine compound of claim 1 wherein R represents a phenylene ring.

4. The tetravinylpyrazine compound of claim 1 wherein X represents a hydrogen atom.

5. The tetravinylpyrazine compound of claim 1 wherein X represents a hydrogen atom and R represents a naphthylene ring.

6. The tetravinylpyrazine compound of claim 1 wherein X represents a hydrogen atom and R represents a pyridinylene ring.

* * * * *